United States Patent [19]

Wenstrup et al.

[11] Patent Number: 5,416,816
[45] Date of Patent: May 16, 1995

[54] CALIBRATION TEMPLATE FOR COMPUTED RADIOGRAPHY

[75] Inventors: Robert B. Wenstrup, Wayland, Mass.; Joseph Fieno, Charlotte, N.C.

[73] Assignee: Boston Test Tool Company, Charlotte, N.C.

[21] Appl. No.: 188,386

[22] Filed: Jan. 27, 1994

[51] Int. Cl.$^6$ .......................................... G01D 18/00
[52] U.S. Cl. ...................................... 378/18; 378/207
[58] Field of Search ................... 378/18, 56, 204, 207, 378/162, 165

[56] References Cited

U.S. PATENT DOCUMENTS

| | | |
|---|---|---|
| 1,953,249 | 4/1934 | Michel . |
| 3,010,223 | 11/1961 | Alderson ........................ 378/207 X |
| 4,044,260 | 8/1977 | Hounsfield . |
| 4,055,771 | 10/1977 | Goodenough et al. . |
| 4,126,789 | 11/1978 | Vogl et al. . |
| 4,280,047 | 7/1981 | Enos . |
| 4,298,799 | 11/1981 | Oliver . |
| 4,323,782 | 4/1982 | Riihimaki et al. . |
| 4,344,183 | 8/1982 | Jacobson . |
| 4,638,502 | 1/1987 | Yaffe . |
| 4,646,334 | 2/1987 | Zerhouni .............................. 378/18 |
| 4,649,561 | 3/1987 | Arnold ............................... 378/207 |
| 4,788,706 | 11/1988 | Jacobson .......................... 378/18 X |
| 4,788,707 | 11/1988 | Malamud et al. . |
| 4,794,631 | 12/1988 | Ridge . |
| 4,818,943 | 4/1989 | Chandra . |
| 4,873,707 | 10/1989 | Robertson ....................... 378/207 X |
| 4,922,915 | 5/1990 | Arnold et al. . |
| 4,980,904 | 12/1990 | Sones et al. ......................... 378/207 |
| 5,056,130 | 10/1991 | Engel .............................. 378/18 X |
| 5,070,454 | 12/1991 | Griffith . |
| 5,236,363 | 8/1993 | Sandrik et al. .................... 378/18 X |

OTHER PUBLICATIONS

Article from magazine "Decisions in Imaging Economics" entitled Pacs in Radiology–A Perspective written by Walter F. Good, David Gur, Carl R. Furman–undated.

Article from magazine "Business Briefs" entitled Siemens/Loral Group Wins Major Military PACs Bid written by Roger M. Lindahl–undated.

Article from magazine "Business Briefs" entitled Armed Forces Pursue PACs Network written by Eric Skjei dated Mar. 1991.

Publication entitled "CR Insights & Images" Editor David A. Stringer–Spring 1993 issue.

Publication entitled "CR Insights & Images" Editor David A. Strigner –Fall 1993 issue.

(List continued on next page.)

*Primary Examiner*—David P. Porta
*Attorney, Agent, or Firm*—Rhodes, Coats & Bennett

[57] ABSTRACT

A calibration for standardizing images taken with X-ray radiation includes an elongated parallelepiped box of dimensions of at least about 14" (35.56 cm) by 17" (43.18 cm), which are the standard dimensions of normal size X-ray film and, computed radiography plates made predominantly of methyl methacrylate and including three sections arranged along the direction of elongation of the box including a thick body section having a first thickness, the sections having imbedded specimens simulating X-ray absorption characteristics of human body portions, including a needle with an eye, step wedge, nylon disks, and copper screens of varying mesh sizes; a thin body section having a thickness less than the first thickness and imbedded pairs of models; and a thoracic body section having a thickness less than the first thickness and including a natural sponge simulating the X-ray absorption characteristics of a human lung and a plurality of air pockets of varying depth in the transmission direction to simulate pneumothoraces on an X-ray film or computed radiography image.

17 Claims, 3 Drawing Sheets

OTHER PUBLICATIONS

Leaflet released from Fuji Medical Systems U.S.A. Inc. entitled "First Computed Radiography Unit Suitable for Use in Mobile Vans is Developed; Use in Rural Areas, Inner-City Clinics and on Battlefield Predicted by Fuji Systems" dated Nov. 20, 1993.

Invited Lecture and Paper entitled "Picture Archiving & Communications Systems (PACs) in Medicine, NATO Advanced Study Institute"; presented by Lieutenant Colonel Fred Goeringer–dated Oct. 14–26, 1990.

Newsletter from Fuji Medical Systems, U.S.A., Inc. entitled: "New CR System Exprected to Provide Expanded Diagnostic Information Introduced By Fuji Medical Systems; System Cuts Radiation, Reduces Re--Takes, Improves Efficiency" editor Banner & Greif, Ltd., dated Nov. 20, 1993.

Article from Magazine "Diagnostic Imaging" entitled "Lasers Shed New Light on Digital Film Recording", written by George J. Whalen and Stuart F. Eckmann–dated Mar. 1986.

Leaflet from "American Roentgen Ray Society" entitled Two-Year Clinical Experience with a Computed Radiography System, written by Kangarloo, et al.–dated Sep. 1988.

Lealet entitled "Siemens–Digiscan Digital Radiography System for Storage Phosphor–Cassette Exposures" written by: Siemens Aktiengesellschaft, Medical Engineering Group undated.

CALIBRATION TEMPLATE FOR COMPUTED RADIOGRAPHY

BACKGROUND OF THE INVENTION

The present invention provides a much needed tool for assisting radiologists and others involved in the field of radiology in understanding computed radiography and in helping computed radiography achieve its full potential.

The use of x-ray imaging apparatus, known as the field of radiology, has been used for many decades; in assisting medical professionals in diagnosing and understanding features internal to the human body. In conventional x-ray radiology, the portion of the patient's body to be examined is interposed between an x-ray radiation source and an unexposed photographic film. The x-rays pass through the patient's body, subject to variable absorption by the varying body parts. The resulting modified x-ray beam exposes the film in a pattern which illustrates internal organs of the patient's body. Bones, of course, absorb more radiation than soft body tissues, and there is variability in the absorption of the x-rays by the various tissue components. This variability is what gives rise to the perceivable image on the film. In conventional x-ray radiology, the photographic film has a chemical emulsion which is developed using conventional chemical processing techniques. That chemical processing technique used in development of the film usually does not vary from one x-ray exposure to another.

In the past ten years or so a new form of radiology has begun to gain acceptance, namely computed radiography. In computed radiography, the film with its chemical emulsion is replaced by a plate having phosphors which are selectively and temporarily altered by the x-ray beam that has passed through the patient. The phosphors are then "read" to provide a digital data record, instead of a film emulsion record. Machines of this type are sold by Fuji Medical Systems USA, Inc., Stamford Conn., USA under the designation FCR TM, by Siemens Medical Systems, Inc. of Iselin, N.J. under the name Digiscan and other manufacturers under various trademarks.

The digital data record can be manipulated using digital data processing techniques, and a visible display can be created on any of several media. The digital processing usually has the objective of enhancing the usefulness of the visual display. A primary digital processing technique, which is virtually universally performed, is an exposure correction routine. The computer evaluates the amount of exposure over the entire image to determine an average black or white value for the image and then adds or subtracts from all of the pixel elements of image to achieve an acceptable image density.

While computed radiography has achieved considerable acceptance, there is still resistance on the part of many radiologists to the use of this new technology. The images created by computed radiography can be fully as illustrative of the patient's conditions as the conventional x-ray film, but will, in many cases have a somewhat different appearance. Radiologists are intensively trained in reading x-ray images made on the conventional film to perceive images and features which the layperson with an untrained eye simply does not see or would not notice without having it pointed out by the trained radiologist. Radiologists used to discerning such fine differences find the different overall appearance of computed radiography images to be so different that they do not have confidence that they can properly read these images, despite the fact that the computed radiography image generally shows all the detail of the x-ray film image. Thus, there is a need in the art for a means to familiarize radiologists with the capabilities of computed radiography and to permit them to gain confidence in the images produced by computed radiography to the level they are already comfortable with for film x-rays.

In addition, one of the important advantages of computed radiography is the fact that the data, being stored in digital form, can be transmitted by a digital data transmission network, whether that be within a hospital or to a remote location over telephone or other transmission lines. Transmission of images in a Picture Archiving and Communication Systems (known by the acronym PACS) over relatively short distances is commonly referred to as a Local Area Network (LAN); distribution of images over a larger distance is usually called a Wide Area Network (WAN); and transmission of images to a remote site is usually called teleradiology. A PACS network can encompass one or more of these image transfer modalities. Computed radiography images can be incorporated into each of these networking systems. By storing and archiving computed radiography images, these images become part of a PACS. The Surgeon General of the military services implemented such a PACS known the Medical Diagnostic Imaging Support (MDIS).

Features of the MDIS include intra-hospital PACS networks which make use of high-speed communication protocol to support high volume image areas such as the radiology department and other selected patient areas such as the hospital emergency room. Hospitals in the military services network are linked by teleradiology systems to permit transmission of data throughout the network, as needed. This enables a hospital to use the services of a remote radiologist to read the computed radiography image, without necessitating travel by the radiologist to the patient's site.

However, radiologists remote from the x-ray exposure facilities may feel reticence about reading the images created from the transmitted digital data, stemming from uncertainty about the quality of the procedures used in making the images or a lack of familiarity with the precise techniques used by the imaging facility. Accordingly, there is a need in the art for a means and method to provide standardization of computed radiography image quality for LAN, WAN, teleradiology and other transmissions of radiographic digital data.

SUMMARY OF THE INVENTION

The present invention fulfills this need in the art by providing a calibration template for standardizing images taken with X-ray radiation including a box made predominantly of a material having an absorption of X-ray radiation simulating the X-ray absorption properties of bone, organs and soft tissue portions of the human body in a variety of x-ray energies used in diagnostic radiology. The box includes a thick body section having a first thickness and imbedded specimens simulating X-ray absorption characteristics of human body portions located in thick portions of human bodies, a thin body section having a thickness less than the first thickness and imbedded models simulating X-ray absorption characteristics of human body portions located in thin portions of human bodies, and a thoracic body section having a thickness less than the first thickness and including a sample simulating the X-ray absorption characteristics of a human lung.

Preferably, at least one of the samples, specimens and models come in pairs of items, to permit comparisons of radiographic images of the items of the pair. Desirably, the samples and specimens are selected from the group consisting of needles with eyes, aluminum step wedges, methyl methacrylate step wedges, nylon disks, holes in the box material of various diameters, and copper screens of varying mesh sizes. In a preferred embodiment the sample simulating X-ray absorption of a human lung is a natural sponge. In a preferred embodiment the box has a transmission direction and the thoracic section has a plurality of air pockets of varying depth in the transmission direction to simulate pneumothoraces on an X-ray film or computed radiography image. Preferably, at least one of the sample, specimen or model includes a cavity formed in the material of the box and grains of rice are located in the cavity.

Preferred materials for the box are methyl methacrylate, polystyrene, styrene, ABS plastic, high density polypropylene, Lexan, and Noryl, with methyl methacrylate most preferred. Typically, the box is an elongated parallelepiped and the three sections are each of substantial area and arranged along the direction of elongation of the box. Preferably, the box has dimensions of at least about 14" (35.56 cm) by 17" (43.18 cm), which are the standard dimensions of normal size X-ray film and computed radiography plates. The box preferably has metal plates in selected ones of the sections to enhance the x-ray absorption of the template.

In a preferred embodiment the thick body section includes about 4 ½ inches (11.43 cm) of methyl methacrylate and 0.250 inches (0.635 cm) of aluminum, the thin body section includes about 2 inches (5.08 cm) of methyl methacrylate and 0.125 inches (0.318 cm) of aluminum, and the thoracic body section includes about 2 inches (5.08 cm) of methyl methacrylate, 0.250 inches (0.635 cm) of aluminum, and 0.030 inch (0.076 cm) of copper.

The invention also provides a method of evaluating the quality of radiographic images including a series of steps. The steps include providing a calibration template having portions simulating the radiographic characteristics of various human body parts, exposing X-ray film with X-rays transmitted through the calibration template, developing the X-ray film to obtain an image viewable by a radiologist, exposing a computed radiography imaging plate with X-rays transmitted through the calibration template, digitally processing the computed radiography imaging plate to obtain an image viewable by a radiologist, and comparing the images from the film and the imaging plate to ascertain if changes in the exposure or the digital processing of the imaging plate are needed to conform the image obtained from the computed radiography with the image obtained from the film.

Preferably, the providing step includes providing a calibration template having multiple sections corresponding to thick, thin and thoracic human body areas, the film exposing and developing steps and the imaging plate exposing and processing steps are performed for a plurality of the multiple sections, and the comparing step is performed for each of the images obtained from the same ones of the sections.

The method may also include digitizing the X-ray film image, and transmitting digital data of the computed radiography image and the digitized X-ray film image over a digital data transmission line to a remote site, reviewer or radiologist.

In a further aspect the invention provides a method of standardizing the properties of computed radiographic images. This method includes distributing calibration templates having portions simulating the radiographic characteristics of various human body parts to a plurality of radiology facilities having computed radiography equipment. At each of the radiology facilities a computed radiography imaging plate is exposed with X-rays transmitted through its calibration template, the plate is digitally processed to obtain an image viewable by a radiologist, and digital data of the computed radiography image is transmitted over a digital data transmission line to a remote site. The images created using received digital data are evaluated to ascertain deviations from a standard, and responsive to evaluation of the transmitted data, the computed radiography equipment which originally provided the image for review is adjusted to minimize discrepancies between the processed image and the standard image. Typically, the evaluating step includes evaluating the images as regards their overall appearance, density, contrast, range, resolution, edge sharpness and conspicuity of image components.

The invention further provides a method of standardizing the quality of computed radiography images. This method begins by distributing computed radiography calibration templates having portions simulating the radiographic characteristics of various human body parts to a plurality of digitized imaging stations having equipment to make images from computed radiography data sets. Then, a computed radiography imaging plate is exposed with X-rays transmitted through the calibration template at a site using standard exposure settings, and the plate is digitally processed with a standard set of imaging parameters to obtain a sample image data set. This sample image data set is transmitted from the site to a selected one, of the remote digitized imaging stations. At the selected remote digitized imaging station, a first image is created using the received sample image data set and a second image is created using standard exposure and imaging parameters of the template. The first and second images are compared to ascertain deviations between them, and the data transmission equipment between the site and the remote imaging station is adjusted to minimize discrepancies between the transmitted processed image and the distributed processed image responsive to evaluation of the transmitted data. Alternatively the first image may be compared to an image made from a stored standard reference calibration data set.

The invention further provides a method of evaluating the quality of radiographic images including the repeated steps of using exposure technique factors to expose x-ray film with x-ray exposure equipment through a calibration template having portions simulating the radiographic characteristics of various human body parts, recording the exposure technique factors, developing the exposed x-ray film, and evaluating the image quality of the x-ray image by assessing the details of patterns for the various body sections simulated with the calibration template. Then later ones of the x-ray images are compared with earlier ones to ascertain needs for improvements in the film, the x-ray exposure equipment or the exposure techniques to ensure optimal image quality. Preferably, the exposure technique factors include the type of x-ray film used, the specific film developing machine used, the developer solution used in developing, the temperature of the developing solution and the replenishment rate of the developing solution.

BRIEF DESCRIPTION OF THE DRAWINGS

The invention will be better understood after a reading of the Detailed Description of the Preferred Embodiments and a review of the drawings in which.

DETAILED DESCRIPTION OF THE PREFERRED EMBODIMENT

The invention provides a calibration template for computed radiography which enables a radiologist to gain confidence in the images produced by computed radiography and also permits remote stations in a PACS to standardize their procedures and exposure methodologies to provide a high confidence level in reading images produced by transmitted digital data of radiographic exposures.

Figure 1:
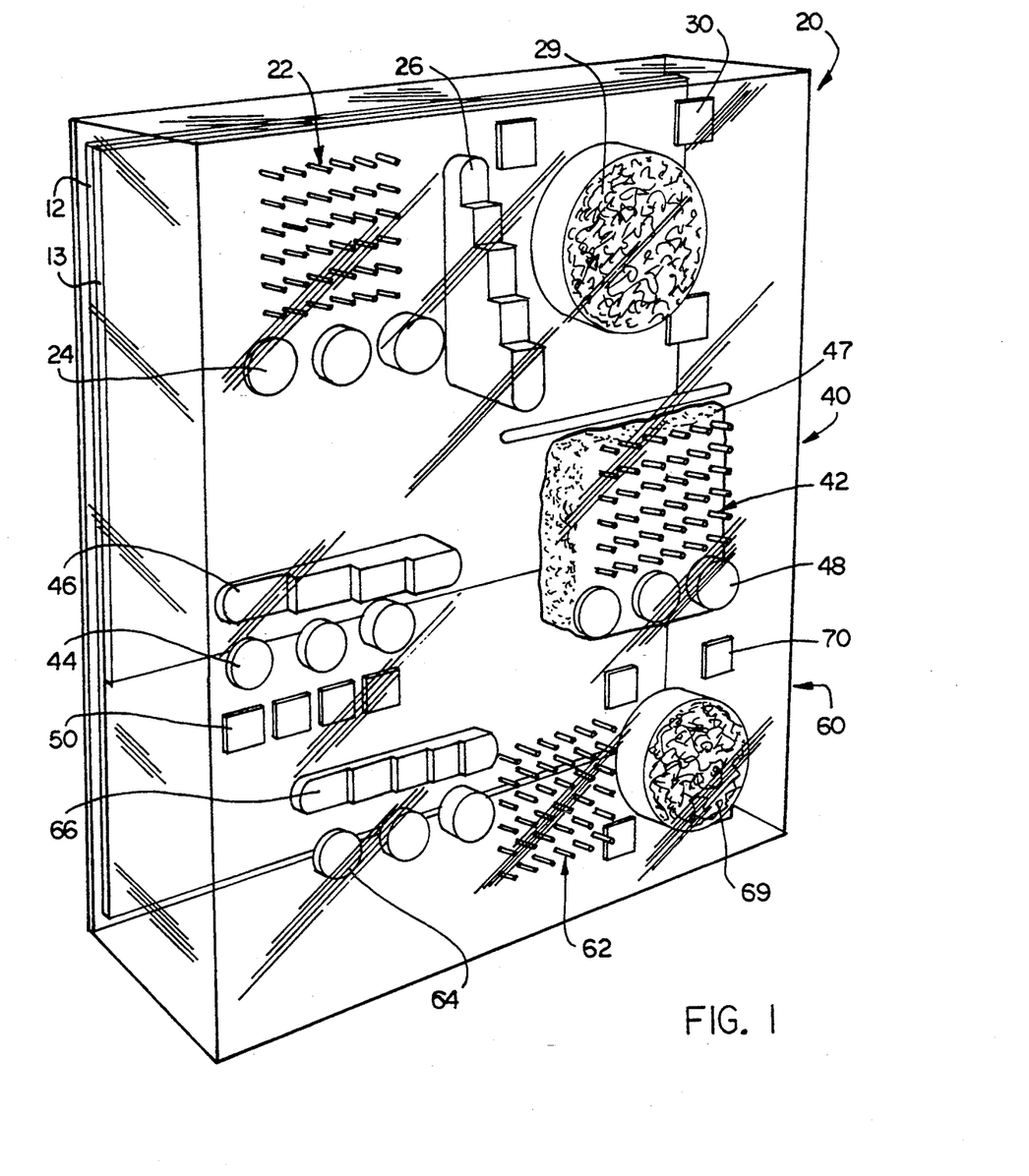
FIG. 1 is a perspective view of a template according to an embodiment of the invention.
Figure 2:
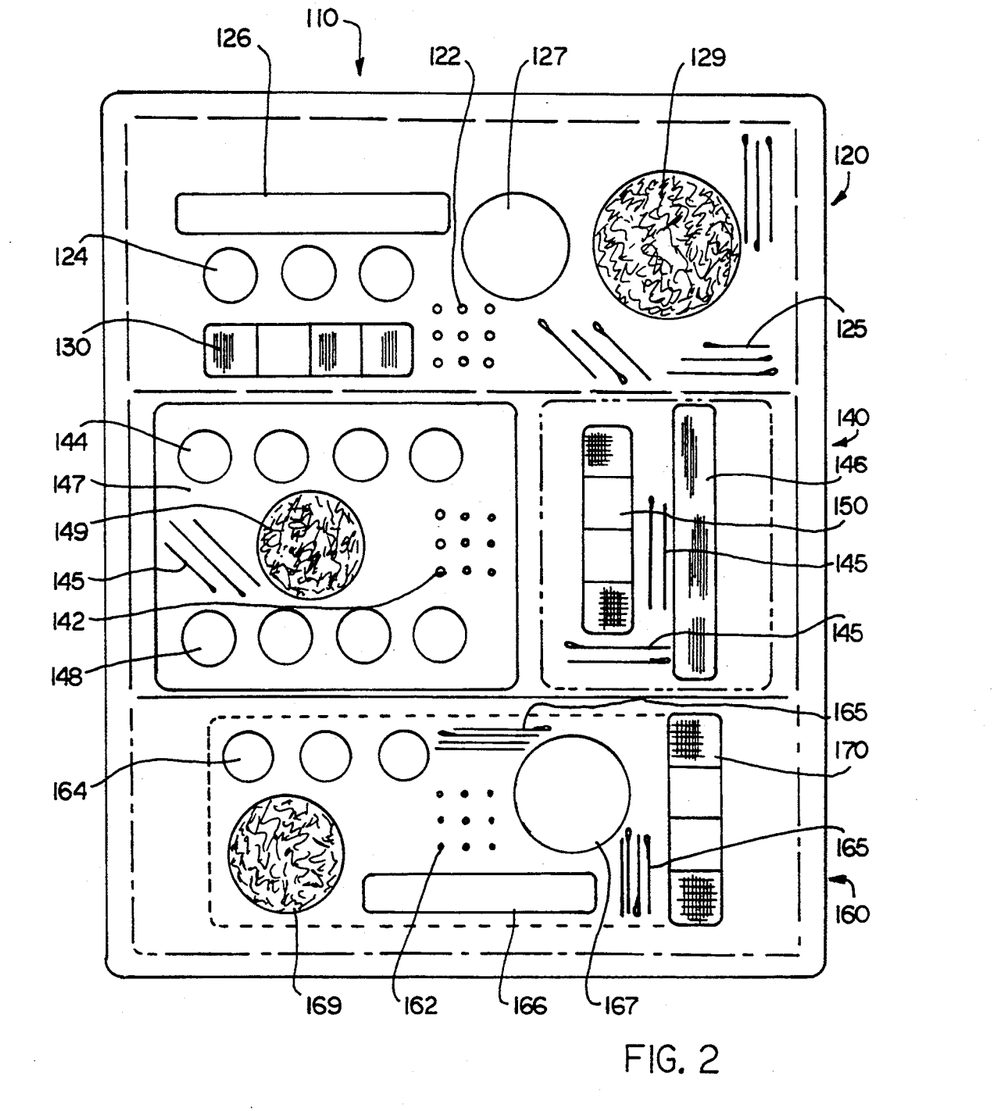
FIG. 2 is an elevation view of a template according to the preferred embodiment.
Figure 3:
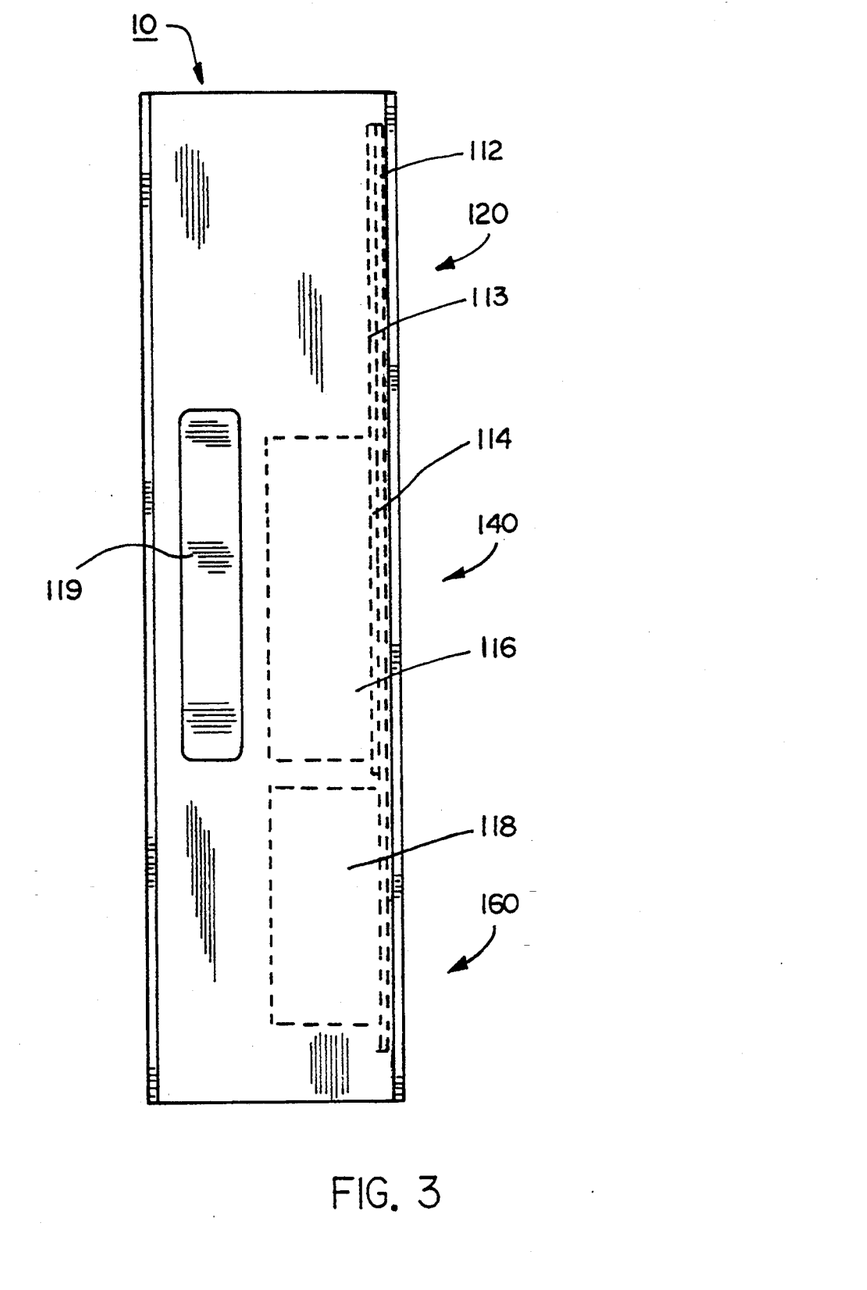
FIG. 3 is a side view of a template according to the embodiment of FIG. 2.

FIG. 1 is a perspective view of an embodiment of a calibration template 10. FIGS. 2 and 3 are elevation and side views of a preferred template 110, which is the same in many respects to the embodiment of FIG. 1. Where the figures include identical or analogous elements, the element will referred to with a reference number 100 larger in FIGS. 2 and 3 than in FIG. 1. The template 10, 110 is preferably in the shape of a right parallelepiped having dimensions of 14" ( 35.56 cm) wide, 17" (43.18 cm) high and 4 ½" (11.43 cm) deep. Having the box of a size of 14"×17" provides a significant benefit, since the template will be used with computed radiography. As was noted above in computed radiography, the pixels of the images are automatically adjusted to obtain an acceptable image density based upon an evaluation of the entire image. Thus, if part of the image is very black or very white, the entire image is affected. By providing the template of a size large enough to cast an image over the entire processing plate, no distortions are introduced.

The template 10, 110 is predominately a box of material having properties of absorption of x-rays with energies of types used for radiography so as to simulate the absorption characteristics of soft tissues of the human body. Suitable materials include methyl methacrylate, polystyrene, styrene, ABS plastic, Lexan, Noryl and high density polypropylene. Polystyrene has good absorption properties, but crazes and cracks easily, so it is not easy to machined. High density polyethylene is suitable, but soft. ABS plastic has suitable absorption characteristics, but clogs up milling bits easily, so it can be difficult to machine. Lexan is similar to methyl methacrylate, but is difficult to obtain in the desired thickness. Noryl is an excellent choice, but cannot be used with oils. Water has desirable absorption characteristics, but is difficult to contain and subject to being spilled. Thus, methyl methacrylate, sold under the trade name Lucite TM is the preferred material.

The template 10, 110 is divided into three sections, including a thick body section 20, 120, a thoracic body section 40, 140 and an extremity body section 60, 160 corresponding to the three major body parts typically differentiated in radiology. This differentiation is based upon the fact that the different body part sections provide somewhat different x-ray absorption and transmittance regimes, and therefore call for different x-ray energies. The thick body part is typically exposed with x-ray energies in the range of 70–90 kvp, a thoracic or chest x-ray is typically exposed above 100 kvp and a body extremities are exposed in the range of 50–60 kvp. Thus, the sections 20, 120, 40, 140 and 60, 160 are designed to have x-ray transmission characteristics at these respective energy levels comparable with those characteristics as present in the typical human body.

The distribution of the material of the box and its dimensions are the same for the embodiments of FIGS. 1-3, but can been more clearly in the views shown in FIGS. 2 and 3. The thick body part section 20, 120 is provided with the methyl methacrylate material for substantially the entire 4½" (11.43 cm) in thickness of the box. Exceptions in thickness exist where materials are to be placed to provide specific x-ray images, as will be discussed further. In addition, sheets of aluminum 12,13 and 112,113 0.250" (0.635 era) thick also covers the thick body section 20, 120, to add to the absorption made possible by the methyl methacrylate so that the thick body section accurately simulates the x-ray absorption of a thick section of the human body.

The thoracic or lung section 30, 130 is provided with a methyl methacrylate thickness of 2" (5.08 cm), plus and extension of plate 12, 112 0.250" (0.635 cm) of aluminum and 14, 114 0.030" (0.076 cm) copper. The thin body section 40 has 2" (5.08 cm) of methyl methacrylate and an extension of aluminum plate 12, 112. It is important that the aluminum and copper be free of high atomic weight impurities which can distort image quality. As seen in FIG. 3, the sections 140, 160 have an air pockets 116, 118 to help fill the volume of the box 110 without attenuating the x-rays as much as would methyl methacrylate. A side recess 119 (with a matching one on the other side of the box 110) serves as a hand grip.

Each of the sections 20, 120,40, 140 and 60, 160 is provided with specimens, models or samples which simulate patterns on x-ray film or computed radiography imaging plates similar to the patterns made by osseous structures, soft tissue and organs radiologists are accustomed to viewing.

Thus, in the thick body section 20, 120 an array of various holes 22, 122 are drilled in a grid pattern, the holes having varying cross-sections. The holes are drilled ½" (1.27 cm) deep, and have diameters ranging from 0.125" (0.318 cm) to 0.029" (0.074 cm). The drilling away of the methyl methacrylate permits the hole to fill with air, which absorbs the x-rays less than the methyl methacrylate. The varying sizes of holes will present different images on the x-ray film or computed radiography image to test the radiologist's ability to see the smallest holes, but typically permitting clear vision of the largest holes. This provides a measure of the degree of resolution of the image.

The section 20, 120 also includes a plurality of nylon plugs 24, 124 one-inch (2.54 cm) in diameter and varying thicknesses in the range of 0.25" (0.635 cm) to 0.75" (1.91 cm). These nylon plugs are embedded in the methyl methacrylate material. It is important that the competed hole not be filled with air, since the only difference sought to be made from the methyl methacrylate absorption is the absorption of the nylon. The nylon inserts in the base simulate large-area low-contrast patterns in each section.

Element 26, 126 is a step wedge made of aluminum inserted in a hole milled in the methyl methacrylate. The step wedge has dimensions of 5¼" (13.33 cm)×¾" (1.91 cm) and has steps of thicknesses ranging from 0.120" (0.305 cm) to 1.375" (3.49 cm). The step-wedges provide a range of densities on the film and computed radiography images. Densitometer measurements of the density of one of the steps of the step wedges in each section can be recorded as a measure of the film system or computed radiography system stability over time.

Item 28, 128 is a hole drilled in the methyl methacrylate and holds a conventional copper scouring pad 29, 129 made up of complex of fine, tortuous, copper strands. The hole for the pad is drilled 3.0" (7.62 cm) in diameter and 1½" (3.81 cm) deep. The copper scouring pad includes a nexus connection which provides a nodal concentration of the copper strands making up the scouring pad. The nexus makes a projected image similar to the infiltrating pattern of cancerous neoplasms. Otherwise, the image made by the scouring pad closely approximates the structure seen in x-rays of human sinuses.

Four copper mesh screens 30, 130 covered with a methyl methacrylate cover plate are also provided. The screens are provided as 1" (2.54 cm) square segments set in drilled-out wells 0.280" (0.711 cm) deep. The 4 screens have mesh sizes of 40, 50, 60 and 80 mesh per inch (2.54 cm). If desired, lead numerals may be placed next to the copper screen segments to identify mesh size. Similarly, such lead indicia may also be located near other features to aid in identification. While the copper mesh is preferred, steel or any other suitable material providing a high frequency, high contrast component compared to the background material could also be used.

It may well be that the scouring pad and/or copper mesh screens can be replaced with an etched copper pattern made using photolithography, a technique conventionally used in making printed circuit boards. This would provide the advantage of increasing the consistency between images made with different templates.

A flat bottomed hole (not shown in FIG. 1, but appearing as item 127 in FIG. 2) is also desirably formed for holding rice grains. The hole is milled 2" (5.08 cm) in diameter and ½" (1.27 cm) deep. The rice grains are held in place with a press-fit methyl methacrylate plug pushed against the rice grains.

Referring now to the thoracic section 40, 140, this also has a plurality of holes 42, 142 similar in virtually all respects to the holes 22, 122 of the thick body section. It also has a plurality of nylon plugs 44, 144 comparable to the nylon plugs 24, 124 of the thick body section, (but varying in thickness from 0.250" (0.64 cm) to 1.00" (2.54 cm)) and a plurality of copper screens 50, 150 identical to the copper screens 30, 130 of the thick body section. The thoracic section 40, 140 also includes a step-wedge 46, 146 similar in all respects to the step-wedge 26, 126 of the thick body section 20, 120.

The lung portion 40 also has in a portion thereof a natural sponge 47, 147, which does an excellent job of simulating lung tissue in x-ray exposures. A plurality of holes 48, 148 are provided 1" (2.54 cm) in diameter and in depths ranging from 0.125" (0.318 cm) up to ½" (1.27 cm) in 0.125" (0,318 cm) increments. The holes 48, 148 are filled with air. The holes 48, 148 and the holes 42, 142 are aligned in the x-ray transmission direction with the sponge 47, 147 so that the discernability of those features as they may appear in lung tissue may be ascertained. The holes 48, 148 are very important as providing images comparable to the images made by pneumothoraces on x-ray film or computed radiography images.

The extremity or thin body section 60, 160 includes many of the similar artifacts previously discussed. Thus, the array of holes 62, 162 are provided the same as the holes 22, 122 and 42, 142. Nylon plugs 64, 164 are identical to nylon plugs 24, 124 and 44, 144, and copper mesh screens 70, 170 are identical to the copper mesh screens 30, 130 and 50, 150. In addition, the thin body section 60, 160 has a drilled-out portion to receive a copper scouring pad 69, 169 like the scouring pad 29, 129 of the thick body section. The thin body section 60, 160 also is provided with step-wedges 66, 166 of methyl methacrylate, rather than the aluminum step-wedges of the other sections. This step-wedge has six steps, three forming cut-outs from the basic 2" (5.08 cm) thickness of the extremity section and two projecting above that surface to form thicknesses greater than 2" (5.08 era). The overall dimensions are ¾" (1.91 cm) wide by 4½" (11.43 cm) long, each step having a width of ¾" (1.91 cm) and vertically rising from its neighbor by ½" (1.27 cm).

In addition, each of the three sections in FIG. 2 is provided with a number of sewing needles 125, 145, 165. The diameters of the needles vary from 0.015" (0.03 cm) to 0.035" (0.089 cm) and length from 1.4" (3.56 cm) to 2.2" (5.59 cm). The exact placement of the needles, and for that matter the other specimens, samples and models, within their respective sections is not critical, except as described herein.

As can be noted, virtually all of the elements provided in each of the sections is provided in multiples in order to provide differential comparison of perception of each set of images made when x-rays are transmitted through the template to make exposures. However, the various ones, such as the holes within a set 22, 42, 62, 122, 142, 162 are made somewhat different from one another, so that there will be differences in the images made, permitting the radiologists to discriminate how much detail is actually visible. These small diameter holes measure the spatial resolution in the presence of scatter.

The needles with small eyes and copper screens of different mesh sizes measure the high frequency, high contrast response of the film and computed radiography plate. Rice patterns imbedded in the methyl methacrylate provide a small-area-low-contrast pattern.

In use, the x-ray technician mounts the template 10, 110 in a position where the patient would normally be located for an x-ray film exposure. The radiographer makes an x-ray exposure using an energy setting typically used for thick body parts such as the pelvis, thoracic body parts (the chest) or extremities such as hands, arms, skull or feet. This step may be repeated for one or both of the other two energies. The three x-ray exposures will have had appropriate energies for one of the respective sections 20, 120, 40, 60, 160 of the tool 10, 110. If procedures have been proper and the x-ray equipment in good order, the x-ray image taken for each respective energy regime should be a good image for the relevant portion of the template 10, 110. Preferably, the exposure technique factors used in the x-ray exposures are recorded, including such things as the type of x-ray film used, the film processing parameters, such as the specific exposing unit used, the developer temperature, replenishment rates, etc. These are well known in the x-ray film exposure art.

The x-ray technologist than repeats the exposures of the template 10, 110 using a computed radiography imaging plate with x-ray exposure techniques (kV, mA, time, distance, focus spot, etc.) similar to the exposure techniques used for the film exposure described above of the thick body section, lung and extremity sections to provide digital data records of the corresponding sections of the template 10, 110. The digital images made using the software settings available with the computed radiography can be compared with the corresponding images made on x-ray film. The radiologist can then examine the two images made of the same template 10, 110 to understand how features exposed on the x-ray film will show on computed radiography. If desired, the radiologist can request changes in the software parameters used during processing to bring the images made using computed radiography into conformance with the images made on x-ray film, or to enhance or reduce edge sharpness, gradient shift, or other properties of the software processing.

In addition, the template 10, 110 can be used to help provide consistent image quality in a PACS. For example, the template can be used for calibration of digitized imaging viewing stations remote from one another. One station with computed radiography equipment or equipment for scanning and digitally transmitting conventional film-derived images can feed its standard image of the thick body section 20, 120, the thoracic section 40,140 or the thin body section 60, 160 made using the template 10, 110 to other sites which have a copy of the standard image on file. On receipt and printing of the transmitted image, each remote site could compare its standard image with the transmitted image to determine the acceptability of the quality of the transmission. Any adjustments necessary to bring transmission into compliance with the accepted standard cart then be made.

X-ray film images of the template 10, 110 can also be made and then digitized using known technology and transmitted to a centralized image interpretation center. Personnel at the interpretation center could print a film copy of the transmitted digitized image and review the film to confirm that the digitized and transmitted data is of acceptable quality and make any necessary adjustments to the scanning, digitizing and transmission. Then, having corrected any errors in the transmission network, actual clinical images can be transmitted for interpretation with a high degree of confidence that conversion and transmission errors will not have corrupted the image.

Alternatively, samples of the template can be distributed to various stations in the network so that each can take computerized radiographic images of the template and generate a standard image. Then, the various terminals in the network can transmit the digital data records of their respective template, and a consensus of an appropriate image can be agreed upon. All of the radiographic imaging stations would then adjust their imaging equipment to make images of the template corresponding to the agreed standard.

The template can also be used for regular quality assurance testing of an existing computed radiography installation to assure that the quality of images being generated does not degrade over time, or to point the way toward re-calibration necessary to bring the images into conformance with the standard.

The template 10, 110 contains specific components which are useful in evaluation of the quality of images used in conventional radiology and radiography, such as spatial resolution, contrast range, low contrast and high contrast detectability. Thus, the exposure response of the film-screen system, exposure consistency and conspicuity of the entire x-ray system composed of x-ray generator, x-ray tube, scatter rejection grid, intensifying screen, x-ray film and film processing equipment may be evaluated. The template 10,110 is also suitable for evaluation and/or routine quality assurance testing of conventional x-ray imaging equipment used for diagnostic radiology for humans, for veterinary medicine, for academic research, and with adjustment of the absorber plates as necessary, for industrial radiography and other imaging systems where photoelectric absorption and Compton scattering of x-rays are used for imaging. Consequently, this template can also be used to assure that the quality of images being generated with these systems does not degrade over time, or to point the way toward recalibration to bring the images back into conformance with accepted quality.

Thus the invention can be implemented as a method of evaluating the quality of radiographic images including the repeated steps of using exposure technique factors to expose x-ray film with x-ray exposure equipment through a calibration template having portions simulating the radiographic characteristics of various human body parts, recording the exposure technique factors, developing the exposed x-ray film, and evaluating the image quality of the x-ray image by assessing the details of patterns for the various body sections simulated with the calibration template. Then later ones of the x-ray images are compared with earlier ones to ascertain needs for improvements in the film, the x-ray exposure equipment or the exposure techniques to ensure optimal image quality. Preferably, the exposure technique factors include the type of x-ray film used, the specific film developing machine used, the developer solution used in developing, the temperature of the developing solution and the replenishment rate of the developing solution.

Those of ordinary skill in the art will appreciate the various modifications to the template and the operating procedures described above may be made while still falling within the scope of the present invention. In particular, numerous variations in the specimens and samples and the respective body part sections of the template can be made.

What is claimed is:

1. A calibration template for standardizing images taken with X-ray radiation comprising
   a box made predominantly of a mate, rial having an absorption of X-ray radiation simulating the X-ray absorption properties of bone, organs and soft tissue portions of the human body in a variety of energies used in diagnostic radiology, said box including
   a thick body section having a first thickness and imbedded specimens simulating X-ray absorption characteristics of human body portions located in thick portions of human bodies,
   a thin body section having a thickness less than said first thickness and imbedded models simulating X-ray absorption characteristics of human body portions located in thin portions of human bodies, and a thoracic body section having a thickness less than the first thickness and including a sample simulating the X-ray absorption characteristics of a human lung.

2. A calibration template as claimed in claim 1 wherein at least one of said samples, specimens and models come in pairs of items, to permit comparisons of radiographic images of said items of said pair.

3. A calibration template as claimed in claim 1 wherein at least one of said samples and specimens is selected from the group consisting of needles with eyes, aluminum step wedges, methyl methacrylate step wedges, nylon disks, holes in the box material of various diameters, and copper screens of varying mesh sizes.

4. A calibration template as claimed in claim 1 wherein each of said samples and specimens includes a needle with an eye, step wedges, nylon disks, and copper screens of varying mesh sizes.

5. A calibration template as claimed in claim 1 wherein said sample simulating X-ray absorption of a human lung is a natural sponge.

6. A calibration template as claimed in claim 1 wherein said predominant material of said box is selected from the group consisting of methyl methacrylate, polystyrene, styrene, ABS plastic, high density polypropylene, Lexan and Noryl.

7. A calibration template as claimed in claim 1 wherein said box is an elongated parallelepiped and said three sections are each of substantial area and arranged along the direction of elongation of said box.

8. A calibration template as claimed in claim 1 wherein said box has dimensions of at least about 14" (35.56 cm) by 17" (43.18 cm), which are the standard dimensions of normal size X-ray film and computed radiography plates.

9. A calibration template as claimed in claim 1 wherein said predominant material of said box is methyl methacrylate.

10. A calibration template as claimed in claim 1 wherein said box has a transmission direction and said thoracic section has a plurality of air pockets of varying depth in the transmission direction to simulate pneumothoraces on an X-ray film or computed radiography image.

11. A calibration template as claimed in claim 1 further comprising metal plates in selected ones of the sections to simulate the x-ray absorption properties of that portion of the human body.

12. A calibration template as claimed in claim 11 wherein said thick body section includes about 4½ inches (11.43 cm) of methyl methacrylate and 0.250 inches (0.635 cm) of aluminum, said thin body section includes about 2½ inches (6.35 cm) of methyl methacrylate and 0.125 inches (0.318) of aluminum, and said thoracic body section includes about 2½ inches (6.35 cm) of methyl methacrylate, 0.250 inches (0.635 cm) of aluminum and 0.032 inches (0.08 cm) of copper.

13. A calibration template as claimed in claim 1 further comprising as one of said sample, specimen or model a cavity formed in the material of said box and grains of rice in said cavity.

14. A calibration template for standardizing images taken with X-ray radiation comprising an elongated parallelepiped box of dimensions of at least about 14" 35.56 cm) by 17" (43.18 cm), which are the standard dimensions of normal size X-ray film and computed radiography plates, said box being made predominantly of methyl methacrylate and including three sections of substantial area arranged along the direction of elongation of said box including a thick body section having a first thickness and imbedded pairs of specimens simulating X-ray absorption characteristics of human body portions located in thick portions of human bodies, including a needle with an eye, a step wedge, nylon disks, copper screens of varying mesh sizes, and a tortuous complex of fine metal strands;

a thin body section having a thickness less than said first thickness and imbedded pairs of models simulating X-ray absorption characteristics of human body portions located in thin portions of human bodies including a needle with an eye, a step wedge, nylon disks, and copper screens of varying mesh sizes; and a thoracic body section having a thickness less than the first thickness and including a natural sponge simulating the X-ray absorption characteristics of a human lung, a needle with an eye, a step wedge, nylon disks, a plurality of air pockets of varying depth in the transmission direction to simulate pneumothoraces on an X-ray film or computed radiography image, copper screens of varying mesh sizes, and a tortuous complex of fine metal strands.

15. A method of evaluating the quality of radiographic images comprising the steps of:

providing a calibration template having portions simulating the radiographic characteristics of various human body parts, exposing X-ray film with X-rays transmitted through the calibration template, developing the X-ray film to obtain an image viewable by a radiologist, exposing a computed radiography imaging plate with X-rays transmitted through the calibration template, digitally processing the computed radiography imaging plate to obtain an image viewable by a radiologist, and comparing the images from the film and the imaging plate to ascertain if changes in the exposure or the, processing of the imaging plate are needed to conform the image obtained from the computed radiography with the image obtained from the film.

16. A method as claimed in claim 15 wherein said providing step comprises providing a calibration template having multiple sections corresponding to thick, thin and thoracic human body areas, said film exposing and developing steps and said imaging plate exposing and processing steps are performed for a plurality of said multiple sections, and said comparing step is performed for each of the images obtained from the same ones of the sections.

17. A method as claimed in claim 15 further comprising digitizing the X-ray film image, and transmitting digital data of the computed radiography image and the digitized X-ray film image over a digital data transmission line to a remote site.

* * * * *